(12) United States Patent
Alkire et al.

(10) Patent No.: US 9,950,108 B2
(45) Date of Patent: Apr. 24, 2018

(54) BAG BALANCER DEVICE AND SYSTEM

(71) Applicant: PRONK TECHNOLOGIES, INC., Sun Valley, CA (US)

(72) Inventors: Gregory Randolph Alkire, Keene, CA (US); Karl A. Ruiter, Honolulu, HI (US)

(73) Assignee: PRONK TECHNOLOGIES, INC., Sun Valley, CA (US)

( * ) Notice: Subject to any disclaimer, the term of this patent is extended or adjusted under 35 U.S.C. 154(b) by 137 days.

(21) Appl. No.: 15/019,832

(22) Filed: Feb. 9, 2016

(65) Prior Publication Data

US 2017/0021091 A1 Jan. 26, 2017

Related U.S. Application Data

(60) Provisional application No. 62/113,668, filed on Feb. 9, 2015.

(51) Int. Cl.
*A61M 5/14* (2006.01)
*F04B 51/00* (2006.01)

(52) U.S. Cl.
CPC ......... *A61M 5/1415* (2013.01); *F04B 51/00* (2013.01); *A61M 2205/3382* (2013.01); *A61M 2205/3393* (2013.01); *A61M 2205/702* (2013.01)

(58) Field of Classification Search
CPC .. A61M 2205/3382; A61M 2205/3393; A61M 2205/702; A61M 5/1415; F04B 51/00
See application file for complete search history.

(56) References Cited

U.S. PATENT DOCUMENTS

| | | | | |
|---|---|---|---|---|
| 4,267,837 A | * | 5/1981 | Purdy | A61M 1/024 604/245 |
| 5,078,699 A | * | 1/1992 | Haber | A61M 5/1408 604/250 |
| 8,567,738 B1 | * | 10/2013 | Adair | A61M 5/1415 128/877 |
| 9,669,155 B2 | * | 6/2017 | Chepurny | A61G 12/008 |
| 2008/0221512 A1 | * | 9/2008 | Da Silva | A61B 5/20 604/65 |
| 2009/0306621 A1 | * | 12/2009 | Thome, Jr. | A61M 5/1408 604/500 |
| 2012/0203204 A1 | * | 8/2012 | Briggs | A61M 5/1412 604/518 |
| 2013/0292521 A1 | * | 11/2013 | Chepurny | A61G 12/008 248/97 |

* cited by examiner

*Primary Examiner* — Francis Gray
(74) *Attorney, Agent, or Firm* — Brooks Acordia IP Law, PC; Pejman Yedidsion; Christopher Weiss (57) ABSTRACT

Systems and devices for maintaining a consistent input fluid height as fluid is consumed during infusion pump testing including a first hook disposed on an end of a first balancer arm; a second hook disposed on an end of a second balancer arm; and an aperture disposed in a connecting member; where the aperture is configured to be a pivot point for the device; and where the device is rotatable between a deployed position and a stored position.

15 Claims, 6 Drawing Sheets

BAG BALANCER DEVICE AND SYSTEM

CROSS-REFERENCE TO RELATED APPLICATIONS

This application claims priority to and benefit of Provisional Patent Application No. 62/113,668 filed Feb. 9, 2015 and is hereby incorporated by reference for all purposes.

TECHNICAL FIELD

The technical field relates to medical testing devices, and more particularly to medical infusion pump testing.

BACKGROUND

Typically, medical infusion pumps need to be tested regularly to ensure that they are performing correctly. Input fluid height is the vertical distance between the input port of the medical infusion pump and the top of the water supply feeding the pump. As liquid is consumed during a test, the input fluid height varies which alters the flow rate of the liquid and reduces testing accuracy.

SUMMARY

Exemplary device embodiments may include: a first balancer arm; a first hook disposed on an end of the first balancer arm; a second balancer arm; a second hook disposed on an end of the second balancer arm; a connecting member, where the first balancer arm may be connected to the connecting member at an end distal from the first hook, and where the second balancer arm may be connected to the connecting member at an end distal from the second hook; and an aperture disposed in the connecting member, where the aperture may be configured to be a pivot point for the device; where the device may be rotatable between a deployed position and a stored position, where the first balancer arm may be positioned at an obtuse angle to the second balancer arm in the deployed position, and where the first hook may be disposed proximate to the second hook in the stored position. Additional exemplary device embodiments may include a ballast bag detachably attached to the second hook. Additional exemplary device embodiments may include a feed bag detachably attached to the first hook, where the feed bag contains a liquid to be output from the feed bag, and where the ballast bag rotates the device about the aperture to maintain a height of an input fluid column of the feed bag within a set range. In additional exemplary device embodiments, the feed bag may be an intravenous (IV) bag. In additional exemplary device embodiments, the ballast bag may be an intravenous (IV) bag. In additional exemplary device embodiments, the first balancer arm may be shorter in length than the second balancer arm, and where the ballast bag may be lighter in weight than an initial weight of the feed bag containing the liquid. In additional exemplary device embodiments, the first balancer arm comprises a first plastic tube, and the second balancer arm comprises a second plastic tube. In additional exemplary device embodiments, the first balancer arm comprises a first hollow aluminum tube, and the second balancer arm comprises a second hollow plastic tube. In additional exemplary device embodiments, at least one of: the first balancer arm and the second balancer arm may be extendable.

Exemplary system embodiments may include a bag balancer apparatus comprising: a first balancer arm; a first hook disposed on an end of the first balancer arm; a second balancer arm; a second hook disposed on an end of the second balancer arm; a connecting member, where the first balancer arm may be connected to the connecting member at an end distal from the first hook, where the second balancer arm may be connected to the connecting member at an end distal from the second hook, and where the first balancer arm may be positioned at an obtuse angle to the second balancer arm; and an aperture disposed in the connecting member, where the aperture acts as a pivot point for the device; a feed bag containing a fluid to be output from the feed bag, where the feed bag may be detachably attached to the bag balancer apparatus via the first balancer arm; a ballast bag, where the ballast bag may be detachably attached to the bag balancer apparatus via the second balancer arm; an infusion pump, where the infusion pump receives the fluid output from the feed bag via a tube; and a test device, where the test device receives an output fluid from the infusion pump; where the ballast bag rotates the bag balancer apparatus about the aperture to maintain an input fluid height of the feed bag within a set range. Additional exemplary system embodiments may include a connector, where a portion of the connector may be disposed through the aperture of the connecting member. In additional exemplary system embodiments, the connector may be an intravenous (IV) pole. In additional exemplary system embodiments, the feed bag may be an intravenous (IV) bag. In additional exemplary system embodiments, the bag balancer apparatus may be rotatable between a deployed position and a stored position, where the first balancer arm may be positioned at an obtuse angle to the second balancer arm in the deployed position, and where the first hook may be disposed proximate to the second hook in the stored position.

Exemplary method embodiments may include: attaching a bag balancer apparatus to a connector at a pivot point of the bag balancer apparatus; attaching a ballast bag to an end of the bag balancer apparatus; attaching a feed bag containing a fluid to be output from the feed bag to an end of the bag balancer apparatus distal from the ballast bag; determining a set range of an input fluid height between an input of an infusion pump and a top of the fluid in the feed bag; adjusting at least one of: the ballast bag weight, a vertical height of the connector, and a vertical height of the input of the infusion pump until the input fluid height may be within the determined set range; and rotating the bag balancer apparatus about the pivot point as the fluid contained in the feed bag may be consumed to maintain the input fluid height within the determined set range.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

Figures 1A, 1B:
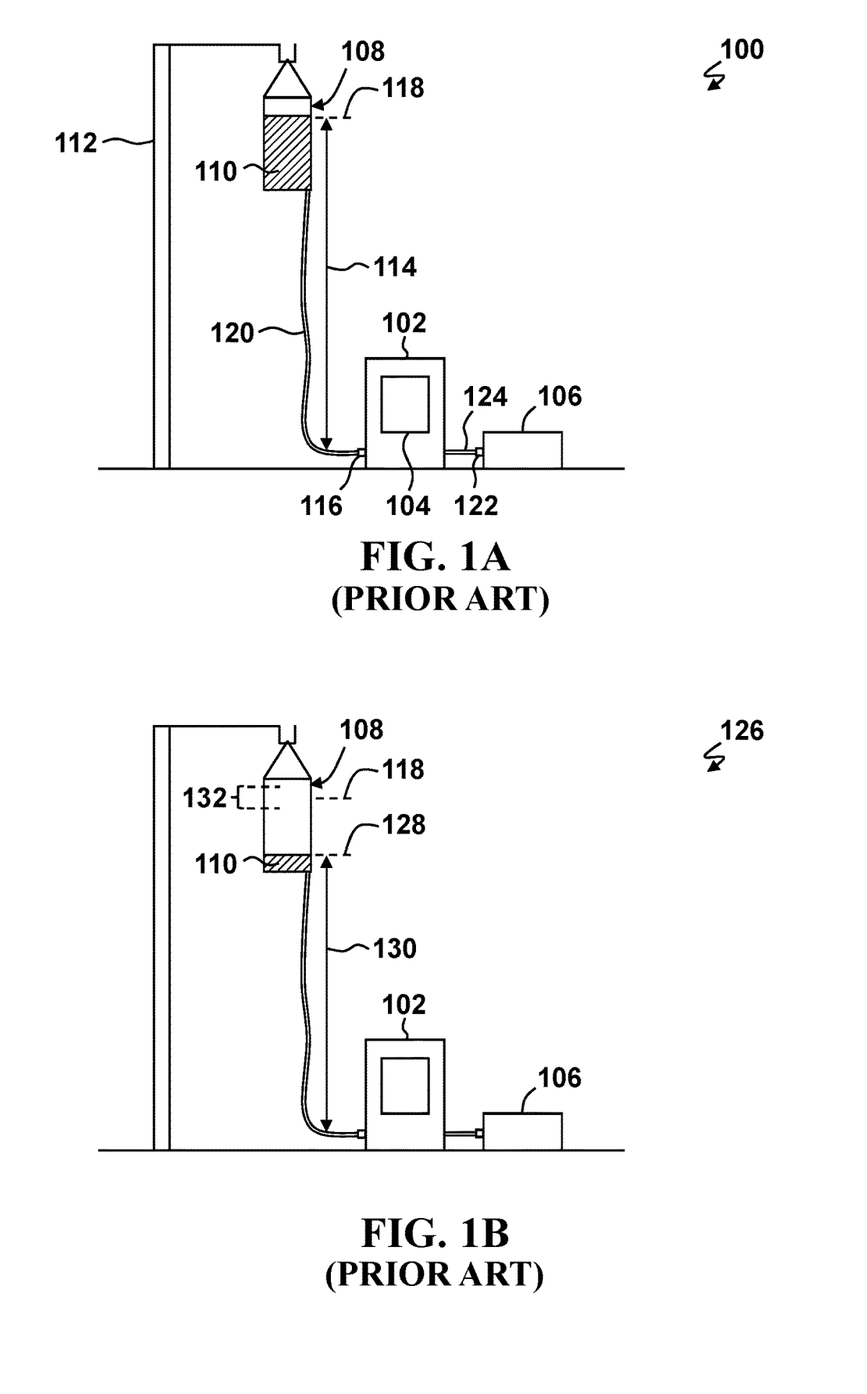
FIG. 1A depicts a conventional testing configuration for an infusion pump at a test starting time.
FIG. 1B depicts the conventional testing configuration of FIG. 1A at a test ending time.

FIG. 1A depicts a conventional testing configuration for an infusion pump at a test starting time 100. A medical infusion pump 102 may administer fluids in small amounts with great precision, e.g., as little as 0.1 mL per hour, and/or in volumes that vary by the time of day, e.g., to match a circadian cycle of a patient. A user may utilize a user interface 104 to set the required mode of the medical infusion pump 102. Due to the precision required, it is imperative that the medical infusion pump 102 is functioning properly. A test device 106 can be used to test the functioning of the medical infusion pump 102 on a regular basis.

An intravenous (IV) bag 108 containing a fluid 110 is suspended by an IV pole 112. The input fluid height 114 is the vertical distance between the input port of the medical infusion pump 116 and the top 118 of the fluid 110 in the IV bag 108. Flow rate of the liquid 110 to the medical infusion pump 102 decreases as the input fluid height 114 decreases. Variation in the input fluid height 114 can have a significant effect on the results of medical infusion pump 102 testing due to the precise amounts of fluids administered by the medical infusion pump 102.

The IV bag 108 feeds fluid 110 to the medical infusion pump 102 via tubing 120. Output from the medical infusion pump 102 is fed to an input 122 of the test device 106, e.g., via tubing 124. The test device 106 tests the performance of the medical infusion pump 102 based on the amount of fluid 110 received from the medical infusion pump 102.

FIG. 1B depicts the conventional testing configuration of FIG. 1A at a test ending time 126. At this point in the testing process, most of the liquid 110 in the IV bag 108 has been consumed. The top 128 of the fluid 110 has decreased from its initial level 118 at the start of the test. Accordingly, the input fluid height 130 has decreased to below a required value. The medical infusion pump 102 manufacturer may set a required range 132 for the input fluid height 130 to avoid potential errors in the testing and/or functioning of the devices. The required range 132 may be +/− one-inch of a desired input fluid height.

Figure 2A:
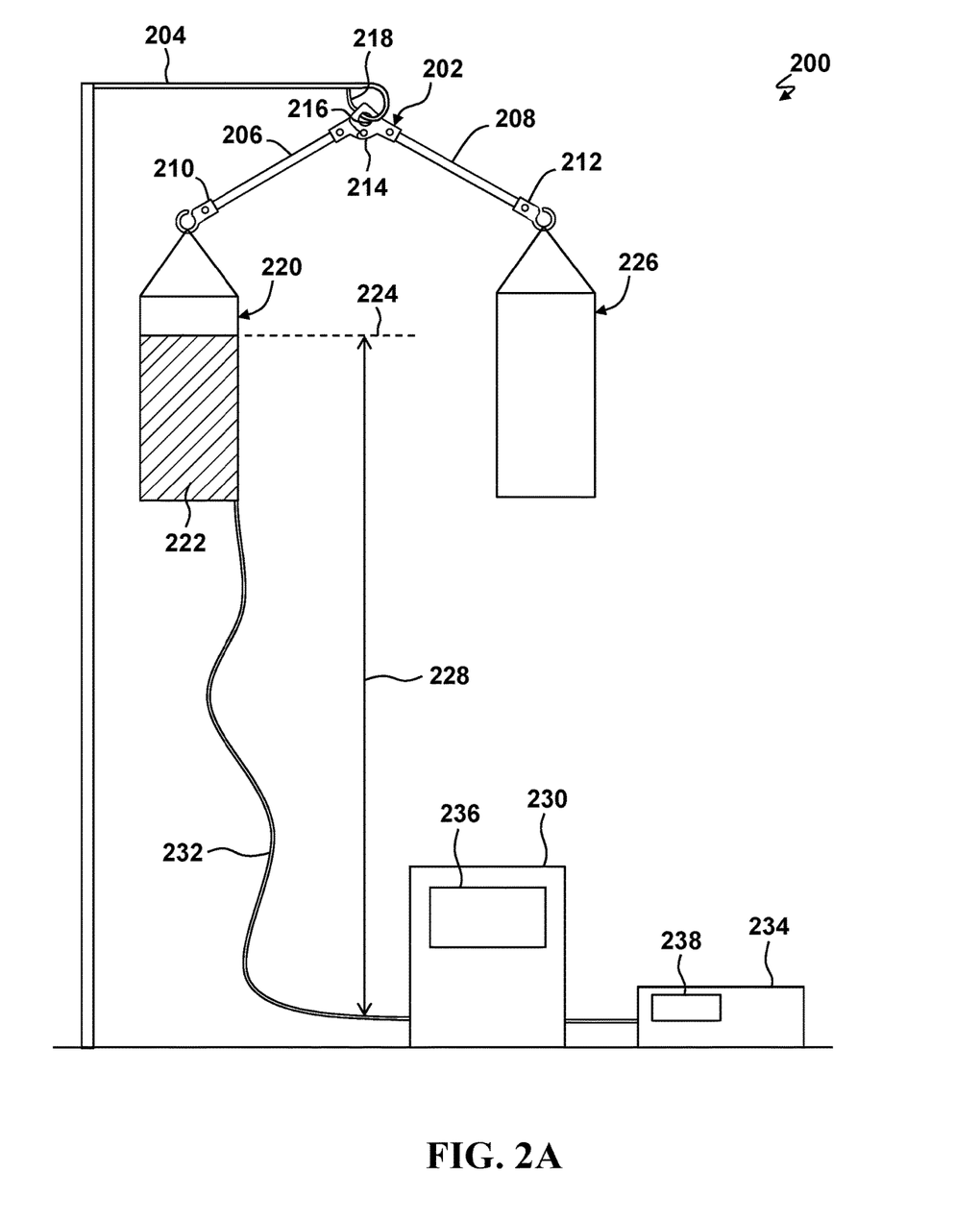
FIG. 2A depicts an embodiment of a testing configuration for an infusion pump using a bag balancer apparatus at a test starting time.

FIG. 2A depicts an embodiment of a testing configuration for an infusion pump using a bag balancer apparatus at a test starting time 200. A bag balancer apparatus 202 is suspended from a support structure, e.g., an IV pole 204. The bag balancer apparatus 202 includes a first balancer arm 206 and a second balancer arm 208. The balancer arms (206, 208) may be comprised of durable plastic and/or hollow aluminum tubes. A first hook 210 is disposed on an end of the first balancer arm 206. A second hook 212 is disposed on an end of the second balancer arm 208. A connecting member 214 joins the first balancer arm 206 and the second balancer arm 208. The first balancer arm 206 is positioned at an obtuse angle to the second balancer arm 208. An aperture 216 is disposed in the connecting member 214. A hook 218 of the IV pole 204 is disposed through the aperture 216 of the connecting member 214, such that the aperture 216 acts as a pivot point for the bag balancer apparatus 202.

A feed bag 220, such as an IV bag, contains a liquid 222 having a fluid height 224. The feed bag may be an IV bag, a bag for a feeding pump, a rigid container, or any other container for holding and dispersing liquid. The feed bag 220 is detachably attached to the bag balancer apparatus 202 via the first hook 210. A ballast bag 226 contains one or more weights to maintain a desired input fluid height 228. In some embodiments, the ballast bag 226 may contain an equal initial amount of fluid as the feed bag 220. The ballast bag may be an IV bag, a bag for a feeding pump, a rigid container, or any other container for holding and dispersing liquid. The ballast bag may be emptied of any liquid for lighter and more compact transport and/or storage. In other embodiments, the ballast bag may contain one or more small weights. The ballast bag 226 is detachably attached to the bag balancer apparatus 202 via the second hook 212. In some embodiments, the ballast bag and/or hook may be replaced by one or more detachably attached weights, e.g., secured via buttons and/or snaps, magnetism, a carabiner, and/or a hook and loop fastener strap.

The feed bag 220 supplies fluid 222 to an infusion pump 230 via tubing 232. The infusion pump then feeds the fluid 222 to a test device 234, e.g., a medical infusion pump tester. The infusion pump 230 and/or test device 234 may have a user interface (236, 238), which may be used to determine a desired input fluid height and/or a set range for the input fluid height to ensure testing and/or operational accuracy. The set range may be +/− one inch of a desired input fluid height.

Figure 2B:
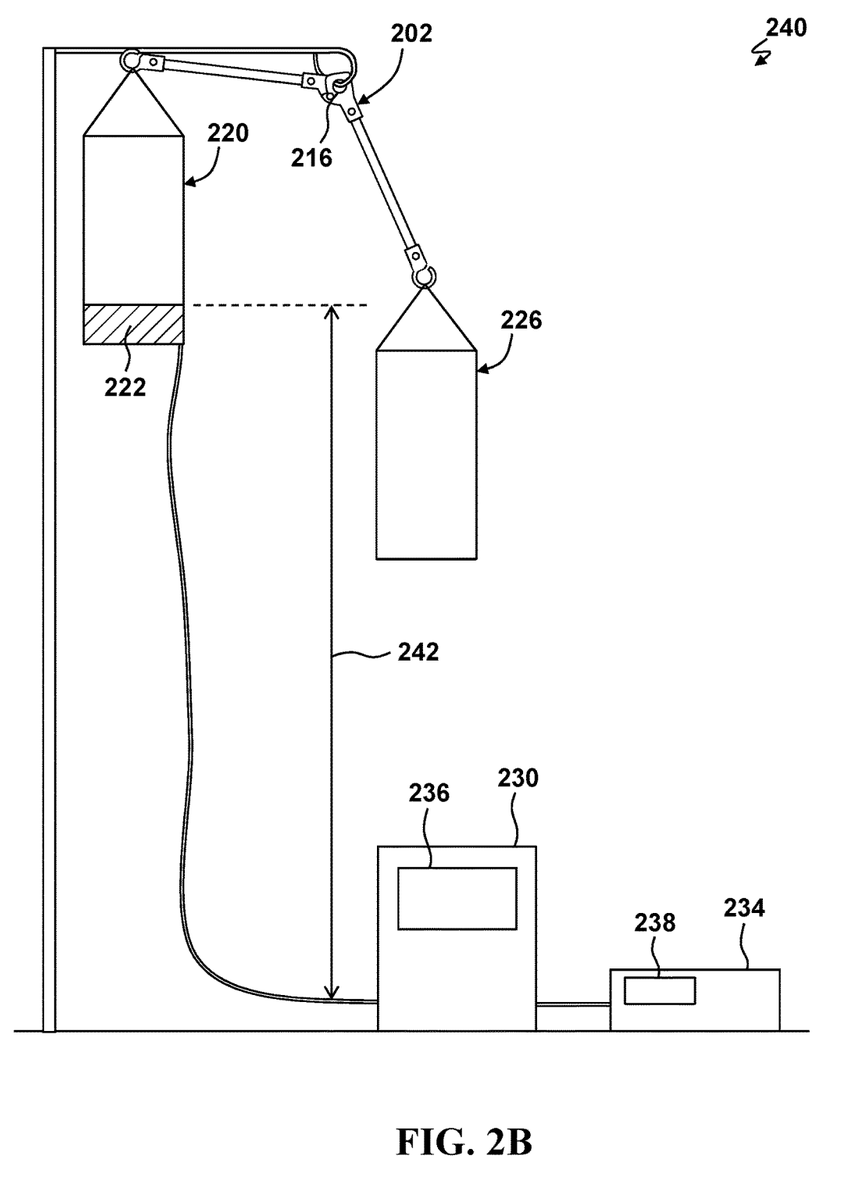
FIG. 2B depicts the embodiment of the testing configuration of FIG. 2A at a test ending time.

FIG. 2B depicts the embodiment of the testing configuration of FIG. 2A at a test ending time 240. A substantial quantity of fluid 222 in the feed bag 220 has been used during testing and only a small quantity remains. The reduction of fluid 222 in the feed bag 220 lowers the weight of the feed bag 220 relative to the ballast bag 226. The increased relative weight of the ballast bag 226 has caused the bag balancer apparatus 202 to rotate about the aperture 216 until the torque created by the ballast bag 226 is matched by the torque created by the feed bag 220. This results in an input fluid height 242 that is substantially the same as the input fluid height at the start of the test (228, See FIG. 2A), and within the set range. The bag balancer apparatus 202 is depicted as suspended from an IV pole via the aperture 216. In other embodiments, alternate detachable and/or permanent attachments may be used as long as they can support the weight of approximately two liters of a liquid, e.g., two one-liter IV bags, and the weight of the bag balancer apparatus 202.

The dynamic movement of the bag balancer apparatus 202, feed bag 220, and ballast bag 226 may allow for prolonged use of the feed bag 220 before needing replacement for falling outside of an acceptable range of input fluid height, a sustained flow rate of fluid 222 from the feed bag 220 to the infusion pump 230, a more accurate administration of fluid 222 by the infusion pump 230, and/or a more accurate testing of the fluid 222 administration via the test device 234. The acceptable range of input fluid height may be specified by the infusion pump 230 manufacturer and/or the test device 234 manufacturer, e.g., within a one-inch margin of error for an input fluid height of twenty inches.

The bag balancer apparatus 202 may include one or more sensors to measure, track, and/or record the position of the bag balancer apparatus 202 relative to a local plane. One or more accelerometers may be placed on a distal end of the bag balancer apparatus 202 to determine the position and/or movement of the bag balancer apparatus 202. A sensor may be used to track input pressure to the infusion pump 230 to ensure that the input fluid height 242 remains within a set range determined by a manufacturer.

In some embodiments, the infusion pump 230 and/or test device 234 may contain a pressure sensor and/or special programming to provide, via a user interface (236, 238), the capability of assessing whether the initial height of the fluid meets the fluid height recommended by the pump manufacturer and/or assists the user in setting up the initial test configuration correctly using pressure values displayed in units relating to water column height, up/down arrows, and/or audio tones. Additionally, the test device 234 may continuously monitor the fluid level and warn the user, e.g., via a visual and/or audio warning, if the fluid level falls below a threshold and outside a range specified by the manufacturer.

In one embodiment, the test device 234 may control the bag balancer apparatus 202 directly using torque to rotate the bag balancer about an axis and, for example, implemented via a series of pulleys to support movement and change of direction of a cable or belt running along the bag balancer apparatus 202. Accordingly, the test device apparatus 202 may assist with the effecting of movement of the input fluid height by lifting loads or applying forces in order to keep the input fluid height consistent in the system. This may also be implemented using one or more sensors that are in direct communication with the circuitry and processor of the test device 234.

Figure 3:
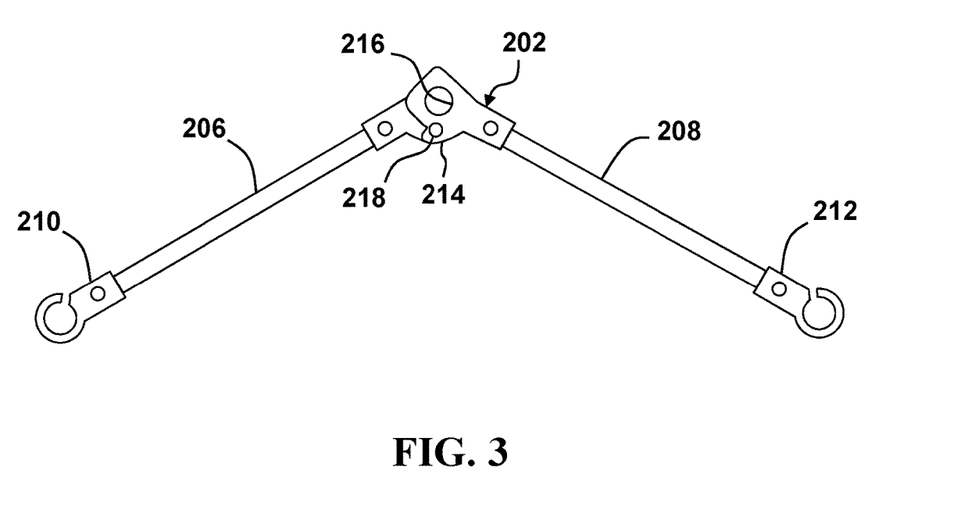
FIG. 3 depicts an exemplary bag balancer apparatus.

FIG. 3 depicts an exemplary bag balancer apparatus 202. The bag balancer apparatus may have a first balancer arm 206, a second balancer arm 208, a first hook 210, a second hook 212, a connecting member 214, and an aperture 216 in the connecting member 214. The balancer arms (206, 208) may be connected to each respective hook (210, 212) and connecting member 214 via a fastener, e.g., a bolt, screw, adhesive, etc. In some embodiments, the balancer arms (206, 208), hooks (210, 212), and a portion of each respective connecting member 214 may be formed as a single part. The connecting member 214 may include two separate components, with each part connected to a respective balancer arm (206, 208) connected at a connector 218, e.g., a bolt. The connector 218 may allow the bag balancer apparatus to rotate between a deployed position and a stored position (See FIG. 6). The two parts of the connecting member 214 may have identical dimensions and/or be mirror images. The length of each balancer arm (206, 208) may vary based on an initial fluid fill height of a feed bag, e.g., each balancer arm (206, 208) may be eight inches in length for use with a feed bag having an initial fluid fill height of six inches. An optimal length of each balancer arm (206, 208) may be 1.62 multiplied by the initial fluid fill height of the feed bag. The angle between the first balancer arm 206 and the second balancer arm 208 may be 130 degrees so as to separate the feed bag from the ballast bag while maintaining bag balancer apparatus 202 dimensions ideal for transport and/or storage.

The first hook 210 and the second hook 212 are used to detachably attach a feed bag and a ballast bag, respectively. In some embodiments, the first hook 210 and/or second hook 212 may be replaced by an alternate detachable attachment, e.g., a magnet, a hook and loop fastener strap, a carabiner, an aperture, etc.

Figure 4:
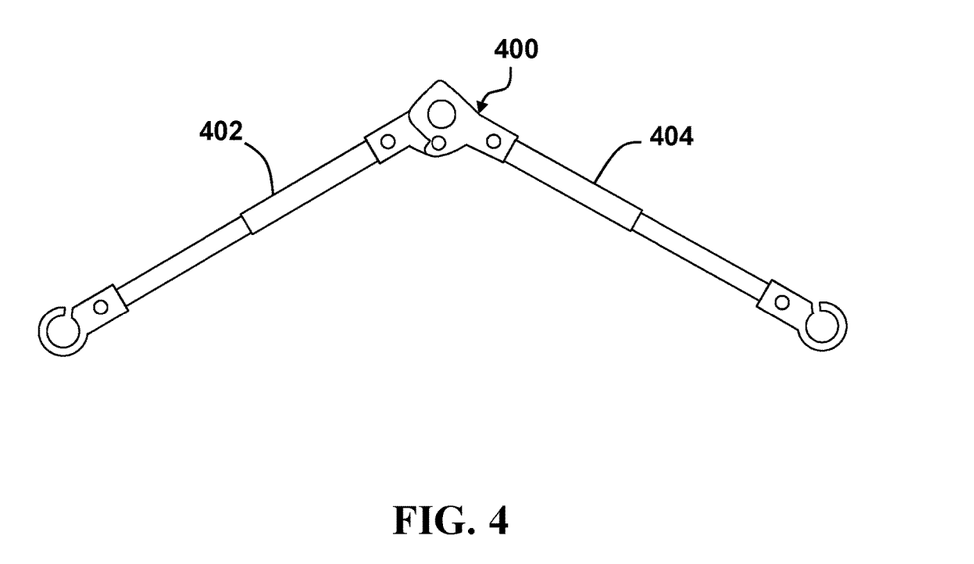
FIG. 4 depicts an exemplary bag balancer apparatus having adjustable length balancer arms.

FIG. 4 depicts an exemplary bag balancer apparatus having adjustable length balancer arms. The bag balancer apparatus 400 may have a first extendable balancer arm 402 and a second extendable balancer arm 404. The extendable balancer arms (402, 404) may be used to shorten or lengthen each respective arm to accommodate various sizes and/or weights of fluid bags and/or ballast bags.

Figure 5:
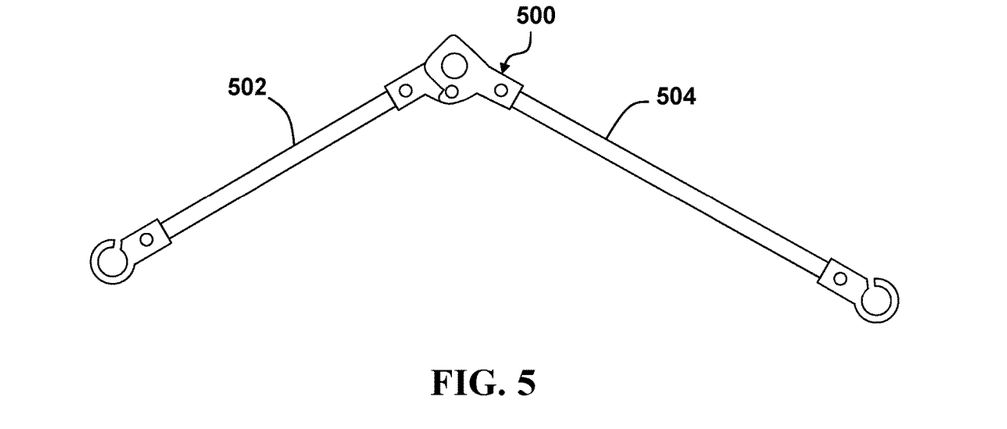
FIG. 5 depicts an exemplary bag balancer apparatus having a longer balancer arm for holding a ballast bag.

FIG. 5 depicts an exemplary bag balancer apparatus having a longer balancer arm for holding a ballast bag. The bag balancer apparatus 400 may have a first balancer arm 502 and a second balancer arm 504. The second balancer arm 504 may be longer than the first balancer arm 502 to accommodate a ballast bag that is lighter than an initial weight of a feed bag.

Figure 6:
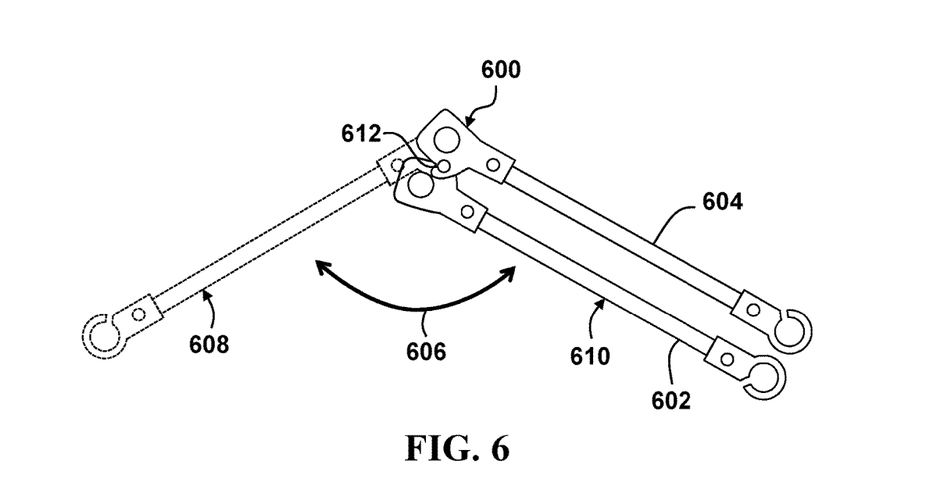
FIG. 6 depicts an exemplary bag balancer apparatus having rotatable balancer arms.

FIG. 6 depicts an exemplary bag balancer apparatus having rotatable balancer arms. The bag balancer apparatus 600 may have a first balancer arm 602 and a second balancer arm 604. The first balancer arm may rotate 606 from a deployed position 608, depicted in dashed lines, to a stored position 610. In the deployed position 608, the first balancer arm 602 is positioned at an obtuse angle to the second balancer arm 604, e.g., 130 degrees. In the stored position 610, the first balancer arm 602 is disposed proximate to the second balancer arm 604. The bag balancer apparatus 600 may be placed into the stored position 610 for transportation and/or storage. The bag balancer apparatus 600 may be constructed from two equal parts that are connected via a connector 612. The connector 612 may be a bolt engaged via a pull, twist, and latch motion to rotate the bag balancer apparatus 600 from the deployed position 608 to the stored position 610, and back to a deployed position 608. The connector 612 may include a spring to force the two sides of the bag balancer apparatus 608 together. The connector 612 may also be a screw, e.g., a wing nut, or other fixed attachments. In some embodiments, the bag balancer apparatus 612 may pivot about the aperture from the deployed position 608 to the stored position 610.

Figure 7:
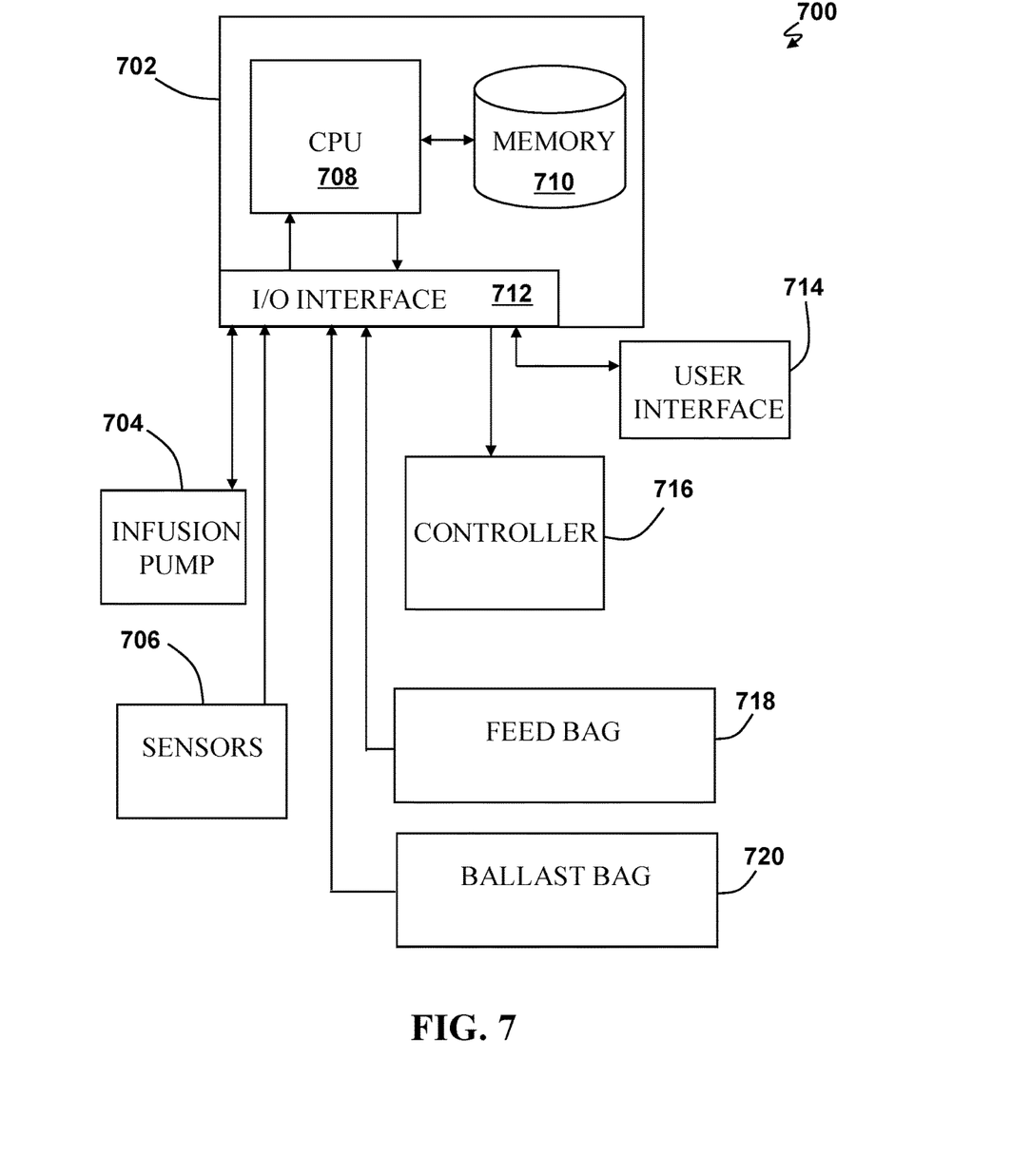
FIG. 7 depicts a functional block diagram of a computing device embodiment.

FIG. 7 depicts a functional block diagram of a computing device embodiment 700. The computing device 702 is connected to an infusion pump 704 and a set of sensors 706, e.g., pressure sensor. The computing device 702 may comprise a central processing unit (CPU) 708 and memory 710, and via an I/O interface 712 configured to, through special programming, provide a user interface 714 for assisting the user with setting up an initial fluid height. The computing device 702 may be capable of the aforementioned functions and optionally effect the adjusting of the fluid height by using a controller 716 and a connection medium to a feed bag 718 and ballast bag 720.

The bag balancer embodiments may be used for many other applications beyond testing infusion pumps. They may be used for gravity infusion (no pump or controller involved) to a patient where precise flow rate is desired. They may be used in conjunction with any infusion pump device using IV bags where a more accurate and precise delivery of medications is desired. Additionally, they may also be used as a low cost alternative to consistently dispense liquids in a laboratory or manufacturing process environment. In all these other applications, the fluid height staying substantially the same throughout the infusion or dispensing has a direct and significant impact on the flow rate precision and accuracy because of the direct relationship between fluid height influence on pressure in that fluid column and subsequent flow rate. In these applications of the different embodiments, the ballast bag may be replaced with small weights and may either hang from the ballast end of the bag balancer or be attached using magnetism.

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further it is intended that the scope of the present invention is herein disclosed by way of examples and should not be limited by the particular disclosed embodiments described above.

What is claimed is:

1. A bag balancer apparatus comprising:
   a first balancer arm;
   a first hook disposed on an end of the first balancer arm;
   a second balancer arm;
   a second hook disposed on an end of the second balancer arm;
   a connecting member, wherein the first balancer arm is connected to the connecting member at an end distal from the first hook, and wherein the second balancer arm is connected to the connecting member at an end distal from the second hook; and
   an aperture disposed in the connecting member, wherein the aperture is configured to be a pivot point for the bag balancer;
   wherein the bag balancer is rotatable between a deployed position and a stored position, wherein the first balancer arm is positioned at an obtuse angle to the second balancer arm in the deployed position, and wherein the first hook is disposed proximate to the second hook in the stored position.

2. The bag balancer apparatus of claim 1 further comprising:
   a ballast bag detachably attached to the second hook.

3. The bag balancer apparatus of claim 2 further comprising:
   a feed bag detachably attached to the first hook, wherein the feed bag contains a liquid to be output from the feed bag, and wherein the ballast bag rotates the bag balancer about the aperture to maintain a height of an input fluid column of the feed bag within a set range.

4. The bag balancer apparatus of claim 3 wherein the feed bag is an intravenous (IV) bag.

5. The bag balancer apparatus of claim 4 wherein the ballast bag is an intravenous (IV) bag.

6. The bag balancer apparatus of claim 3 wherein the first balancer arm is shorter in length than the second balancer arm, and wherein the ballast bag is lighter in weight than an initial weight of the feed bag containing the liquid.

7. The bag balancer apparatus of claim 1 wherein the first balancer arm comprises a first plastic tube, and wherein the second balancer arm comprises a second plastic tube.

8. The bag balancer apparatus of claim 1 wherein the first balancer arm comprises a first hollow aluminum tube, and wherein the second balancer arm comprises a second hollow plastic tube.

9. The bag balancer apparatus of claim 1 wherein at least one of: the first balancer arm and the second balancer arm is extendable.

10. A system comprising:
    a bag balancer apparatus comprising:
      a first balancer arm;
      a first hook disposed on an end of the first balancer arm;
      a second balancer arm;
      a second hook disposed on an end of the second balancer arm;
      a connecting member, wherein the first balancer arm is connected to the connecting member at an end distal from the first hook, wherein the second balancer arm is connected to the connecting member at an end distal from the second hook, and wherein the first balancer arm is positioned at an obtuse angle to the second balancer arm; and
      an aperture disposed in the connecting member, wherein the aperture acts as a pivot point for the bag balancer apparatus;
    a feed bag containing a fluid to be output from the feed bag, wherein the feed bag is detachably attached to the bag balancer apparatus via the first balancer arm;
    a ballast bag, wherein the ballast bag is detachably attached to the bag balancer apparatus via the second balancer arm;
    an infusion pump, wherein the infusion pump receives the fluid output from the feed bag via a tube; and
    a test device, wherein the test device receives an output fluid from the infusion pump;
    wherein the ballast bag rotates the bag balancer apparatus about the aperture to maintain an input fluid height of the feed bag within a set range.

11. The system of claim 10 further comprising:
    a connector, wherein a portion of the connector is disposed through the aperture of the connecting member.

12. The system of claim 11 wherein the connector is an intravenous (IV) pole.

13. The system of claim 10 wherein the feed bag is an intravenous (IV) bag.

14. The system of claim 10 wherein the bag balancer apparatus is rotatable between a deployed position and a stored position, wherein the first balancer arm is positioned at an obtuse angle to the second balancer arm in the deployed position, and wherein the first hook is disposed proximate to the second hook in the stored position.

15. A method comprising:
    attaching a bag balancer apparatus to a connector at a pivot point of the bag balancer apparatus;
    attaching a ballast bag to an end of the bag balancer apparatus;
    attaching a feed bag containing a fluid to be output from the feed bag to an end of the bag balancer apparatus distal from the ballast bag;
    determining a set range of an input fluid height between an input of an infusion pump and a top of the fluid in the feed bag;
    adjusting at least one of: the ballast bag weight, a vertical height of the connector, and a vertical height of the input of the infusion pump until the input fluid height is within the determined set range; and
    rotating the bag balancer apparatus about the pivot point as the fluid contained in the feed bag is consumed to maintain the input fluid height within the determined set range.

* * * * *